United States Patent
Tanaka (10) Patent No.: US 12,239,576 B2
(45) Date of Patent: Mar. 4, 2025

(54) STENT

(71) Applicant: Yamaga CL LLC, Yamaga (JP)

(72) Inventor: Kengoh Tanaka, Yamaga (JP)

(73) Assignee: Yamaga CL LLC, Kumamoto (JP)

( * ) Notice: Subject to any disclaimer, the term of this patent is extended or adjusted under 35 U.S.C. 154(b) by 237 days.

(21) Appl. No.: 17/278,338

(22) PCT Filed: Dec. 3, 2019

(86) PCT No.: PCT/JP2019/047179
§ 371 (c)(1),
(2) Date: Mar. 22, 2021

(87) PCT Pub. No.: WO2020/116433
PCT Pub. Date: Jun. 11, 2020

(65) Prior Publication Data
US 2021/0346201 A1    Nov. 11, 2021

(30) Foreign Application Priority Data

Dec. 4, 2018  (JP) ................................ 2018-227701

(51) Int. Cl.
*A61F 9/007*        (2006.01)
*A61M 39/24*       (2006.01)

(52) U.S. Cl.
CPC ......... *A61F 9/00781* (2013.01); *A61M 39/24* (2013.01); *A61F 2210/0014* (2013.01)

(58) Field of Classification Search
CPC .. A61F 9/00781; A61F 9/007; A61F 9/00772; A61F 2/82; A61F 2210/0014; A61F 2210/00; A61M 39/24
See application file for complete search history.

(56) References Cited

U.S. PATENT DOCUMENTS

| | | | | |
|---|---|---|---|---|
| 6,113,567 A | * | 9/2000 | Becker | A61F 9/00772 604/265 |
| 2010/0179468 A1 | * | 7/2010 | Becker | A61M 31/00 604/8 |
| 2013/0267887 A1 | * | 10/2013 | Kahook | A61F 9/00781 604/9 |
| 2017/0216094 A1 | * | 8/2017 | Reo | A61M 27/002 |

(Continued)

FOREIGN PATENT DOCUMENTS

| | | |
|---|---|---|
| CN | 203777102 U | 8/2014 |
| JP | WO02/014577 A | 2/2002 |

(Continued)

OTHER PUBLICATIONS

International Search Report of International Patent Application No. PCT/JP2019/047179 completed Jan. 21, 2020 and mailed Feb. 4, 2020 (5 pages).

(Continued)

*Primary Examiner* — Ariana Zimbouski
*Assistant Examiner* — Timothy L Flynn
(74) *Attorney, Agent, or Firm* — Pyprus Pte Ltd; George D. Liu (57) ABSTRACT

To provide a stent capable of preventing reclosing granulation. Provided is a stent including a cylindrical body part 3 and a tip portion 5 positioned at the tip of the body part 3, wherein the closer to the tip the tip portion 5 gets, the larger the width of the tip portion 5 becomes.

10 Claims, 7 Drawing Sheets

(56) References Cited

U.S. PATENT DOCUMENTS

| | | | | |
|---|---|---|---|---|
| 2018/0000616 A1* | 1/2018 | Siersema | ................ | A61F 2/852 |
| 2020/0170778 A1* | 6/2020 | Ehnes | ....................... | A61F 2/88 |
| 2020/0368017 A1* | 11/2020 | Hofferberth | .......... | A61F 2/2418 |

FOREIGN PATENT DOCUMENTS

| | | |
|---|---|---|
| JP | 2004-89696 A | 3/2004 |
| JP | 2004-230012 A | 8/2004 |
| JP | 2005-328922 A | 12/2005 |
| JP | 4510511 B | 7/2010 |
| JP | 2016-209609 A | 12/2016 |

OTHER PUBLICATIONS

Written Opinion of International Patent Application No. PCT/JP2019/047179 completed Jan. 21, 2020 and mailed Feb. 4, 2020 (3 pages).

* cited by examiner

STENT

TECHNICAL FIELD

The present invention relates to a stent. More specifically, the present invention relates to a stent that is used, for example, as a nasolacrimal duct stent.

BACKGROUND ART

JP4510511B discloses a lacrimal passage stent having a disk-like reinforcing member. This lacrimal passage stent is a modified version of a brim NST.

CITATION LIST

Patent Literature

PTL 1: JP4510511B

SUMMARY OF THE INVENTION

Technical Problem

The above lacrimal passage stent is basically intended to be removed on a regular basis because granulation may cause reocclusion. An object of the present invention is to provide a stent that can prevent reocclusion caused by granulation.

Solution to Problem

The above problem can be solved by using a stent with a wide tip to prevent reocclusion caused by granulation.

The present invention relates to a stent. The stent comprises a tubular body part 3 and a tip portion 5 located at the tip of the body part 3. The tip portion 5 becomes wider toward the tip. The body part 3 preferably has a mesh-like shape. The tip portion 5 preferably has an irregular surface (particularly on the body surface side), and the tip portion 5 also preferably has a mesh-like shape. Examples of the stent include stents for use in the field of ophthalmology, including nasolacrimal duct stents; stents for use in the field of brain surgery, including cerebral aqueduct stents; stents for use in the field of otolaryngology, including eustachian tube stents; stents for use in digestive organs, including bile duct stents and anal stents; stents for use in the field of urology, including ureteral stents; stents for use in the field of gynecology and obstetrics, including fallopian tube stents; and stents for use in the respiratory field.

The stent preferably comprises an imaging unit 6 in the tip portion 5. The imaging unit 6 is a part that allows visual recognition when imaging is performed from the outside after the stent is placed inside the body.

The stent preferably has one or more external stoppers 7 on the outer periphery of the body part 3.

The stent preferably has a backflow prevention mechanism 9 on the inner periphery of the body part 3.

The stent preferably further has a lower portion 15 (lower tip portion) located at the bottom of the body part 3.

In the stent, a connecting part 19 that connects the body part 3 to the tip portion 5 is preferably a shape memory part.

In the stent, the body part 3 preferably has an extension part 21 extending from the tip portion 5, and the extension part 21 preferably has, at its tip, a tip part 23 that forms a curved surface and that is harder than the body part 3.

This specification also provides a kit comprising any of the above stents and a stent guide 25. The stent guide 25 is inserted into the body part 3 and guides the stent to the target location. The stent guide 25 has a blade 27 on the inner surface of its tip.

Advantageous Effects of the Invention

The above problem can be solved by using a stent with a wide tip to prevent reocclusion caused by granulation.

BRIEF DESCRIPTION OF THE DRAWINGS

FIG. 6A shows a cross-sectional view of the tip part of the suction tube, and FIG. 6B shows an X-X cross-sectional view of FIG. 6A.

FIG. 7A shows an example of a cutting blade part extending at an angle upward from the direction perpendicular to the central axis of the suction tube body part, and FIG. 7B shows an example of a cutting blade part extending at an angle downward from the direction perpendicular to the central axis of the suction tube body part.

FIG. 9A is a conceptual diagram of the suction tube being divided in half. FIG. 9B is a view of the suction tube of FIG. 9A viewed from above.

FIG. 10A shows a conceptual diagram of the suction tube viewed from above, FIG. 10B shows an X-X cross-sectional view of FIG. 10A, and FIG. 10C shows a Y-Y cross-sectional view of FIG. 10A.

DESCRIPTION OF THE EMBODIMENTS

Modes for carrying out the present invention will be described below with reference to the drawings. The present invention is not limited to the modes described below, and includes those appropriately modified by a person skilled in the art within a scope obvious from the following modes.

Figure 1:
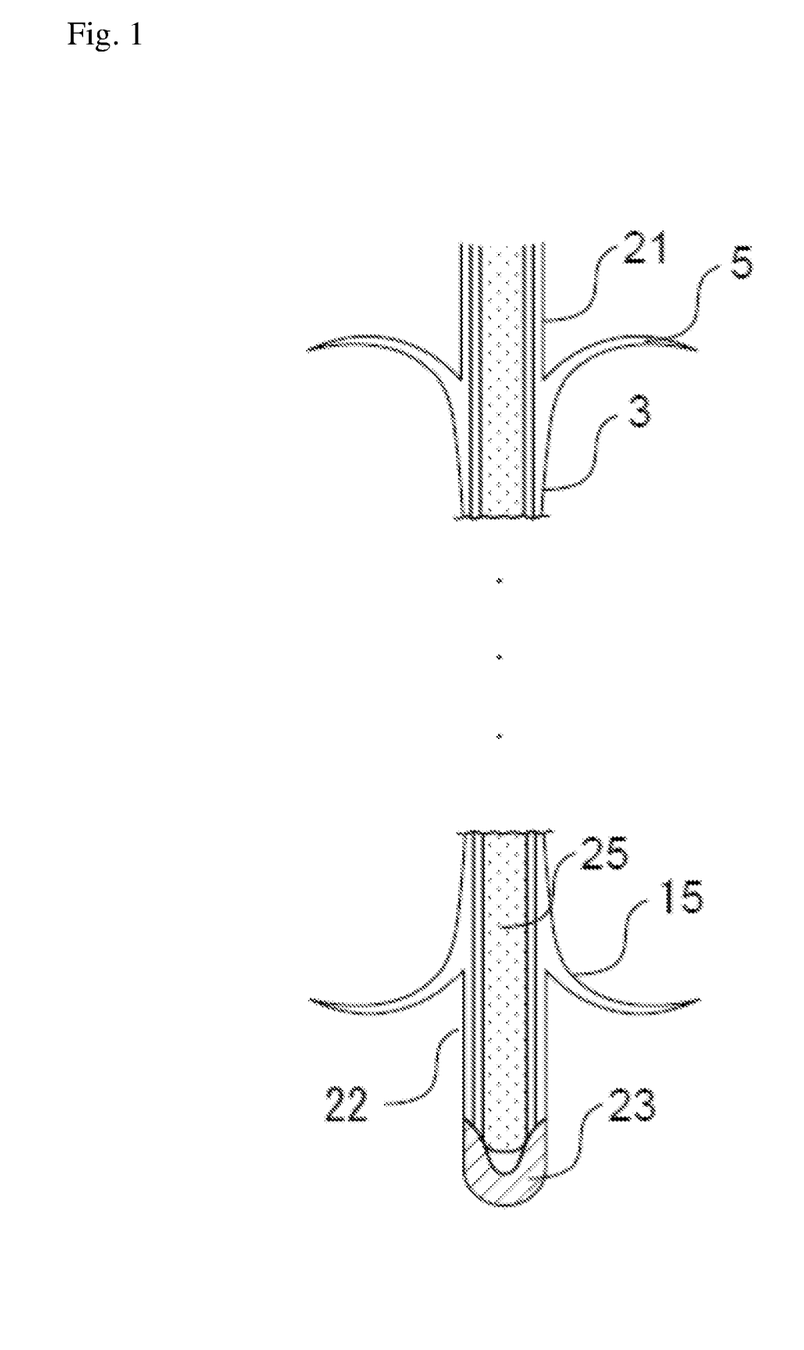
FIG. 1 is a conceptual diagram showing an example of the stent of the present invention.

FIG. 1 is a conceptual diagram showing an example of the stent. As shown in FIG. 1, the stent comprises a tubular body part 3 and a tip portion 5 located at the tip of the body part 3. Examples of the stent include stents for use in the field of ophthalmology, including nasolacrimal duct stents, conjunctival nasal cavity stents, and conjunctival lacrimal stents; stents for use in the field of brain surgery, including Monro foramen stents and cerebral aqueduct stents; stents for use in the field of otolaryngology, including eustachian tube stents; stents for use in the field of urology, including bile duct stents; stents for use in digestive organs, including anal stents; stents for use in the field of urology, including ureteral stents; and stents for use in the field of gynecology and obstetrics, including fallopian tube stents; and stents for use in the respiratory field. When the stent is a nasolacrimal duct stent for nasolacrimal duct, the diameter thereof is, for example, 2 mm or more and 8 mm or less, and may be 3 mm or more and 7 mm or less, or 4 mm or more and 6 mm or less. Hereinafter, a lacrimal stent will be mainly described. The body part 3 is the main body of the stent to be placed in the body. The tip portion is a portion into which the stent is inserted. In the case of a lacrimal stent, the tip portion is located in the upward direction. A nasolacrimal duct stent is a stent to be placed in the nasolacrimal duct.

The tip portion 5 becomes wider toward the tip. The tip means a tip direction, and in the case of a lacrimal stent, the tip direction is the upward direction or downward direction. Since the tip portion 5 becomes wider toward the tip as described above, occlusion caused by granulation can be prevented after the stent is placed. The tip portion 5, which becomes wider toward the tip, may be present at both ends of the stent, or may be present at only one end. The diameter (maximum diameter) of the tip portion 5 (when having a circular outer periphery) is, for example, 1.05 times to 2 times the diameter of the body part 3 (when having a circular outer periphery), and may be 1.5 times to 2 times, 1.6 times to 1.9 times, 1.1 times or more and 1.3 times or less, or 1.2 times or more and 1.3 times or less. The tip portion 5 may have a circular shape with a diameter gradually increasing toward the tip, like a petal, or may be oval or rugby ball-shaped. From the viewpoint of preventing granulation and preventing removal due to frictional resistance, the tip portion 5 preferably has an irregular surface (particularly on the body surface side), and the tip portion 5 may have a mesh-like shape.

The example shown in FIG. 1 has an extension part 21 extending from the tip portion 5. The tip of the extension part 21 may be configured to become narrower toward the tip. The tip of the extension part 21 may have a tubular shape with the same width as the body part, or may be tapered.

As the body part 3, one similar to that of a known lacrimal stent can be used. On the other hand, from the viewpoint of ensuring tissue metabolism, the body part 3 preferably has a mesh-like shape. If the body part 3 is occluded, metabolism such as respiration of the tissue in close contact with the body part 3 is inhibited. For the mesh-like shape, a known structure used for a known stent can be adopted. The body part 3 may have a plurality of holes. The body part 3 may be formed from a shape memory alloy.

Figure 2:
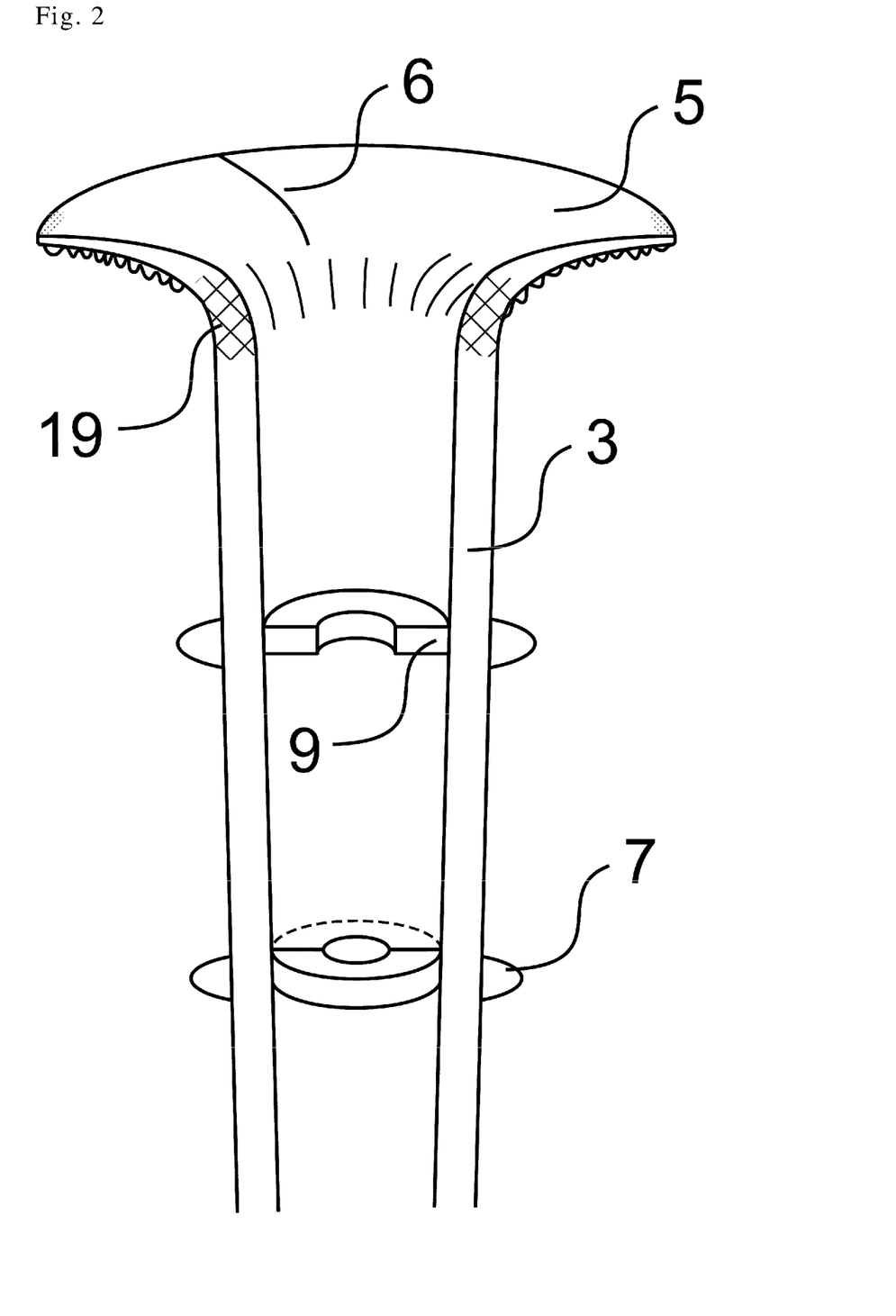
FIG. 2 is a conceptual diagram showing an example of the stent of the present invention.

FIG. 2 is an enlarged example of the tip portion of the stent. The stent preferably comprises an imaging unit 6 in the tip portion 5. The imaging unit 6 is a part that allows visual recognition when imaging is performed from the outside after the stent is placed inside the body. An example of the imaging unit 6 is a marker based on barium sulfate. Due to the presence of the imaging unit 6, the position of the stent and the state of occlusion caused by granulation can be grasped. For example, when the tip portion 5 is covered with granulation, the marker becomes less clear than when it is not covered with granulation. This allows the doctor to recognize that it is time to replace this stent. The imaging unit 6 may be the whole or a part of the tip portion 5.

The stent preferably has one or more external stoppers 7 on the outer periphery of the body part 3. An example of the external stopper is a ring provided on the outer periphery of the body part 3. There may be one ring or multiple rings. The width of the ring may be adjusted as appropriate depending on the shape of the stent. The external stopper is preferably larger than the diameter of the body part (when having a circular outer periphery) and smaller than the diameter (maximum diameter) of the tip portion 5. The width of the external stopper is, for example, 0.01 mm or more and 5 mm or less, and may be 0.1 mm or more and 2 mm or less. The presence of such an external stopper prevents the displacement of the placed stent. Of course, the stopper is an optional element, and may not be present.

The stent preferably has a backflow prevention mechanism 9 on the inner periphery of the body part 3. The presence of the backflow prevention mechanism 9 makes it possible to prevent backflow of liquid in the stent. As an example of the backflow prevention mechanism 9, semicircular parts with hollow insides are alternately present. In FIG. 1, the backflow prevention mechanism 9 at the tip is in contact with the inner surface of the body part in the back, and the backflow prevention mechanism 9 at the bottom is in contact with the inner surface of the body part in the front. Of course, the backflow prevention mechanism 9 is an optional element, and may not be present. When the inside of this element is removed, it is easier to place the stent using a guide 25, described later. The width of the backflow prevention mechanism 9 may be adjusted as appropriate depending on the size of the stent. The width of the backflow prevention mechanism 9 is, for example, 0.01 mm or more and 5 mm or less, and may be 0.1 mm or more and 2 mm or less.

Figure 3:
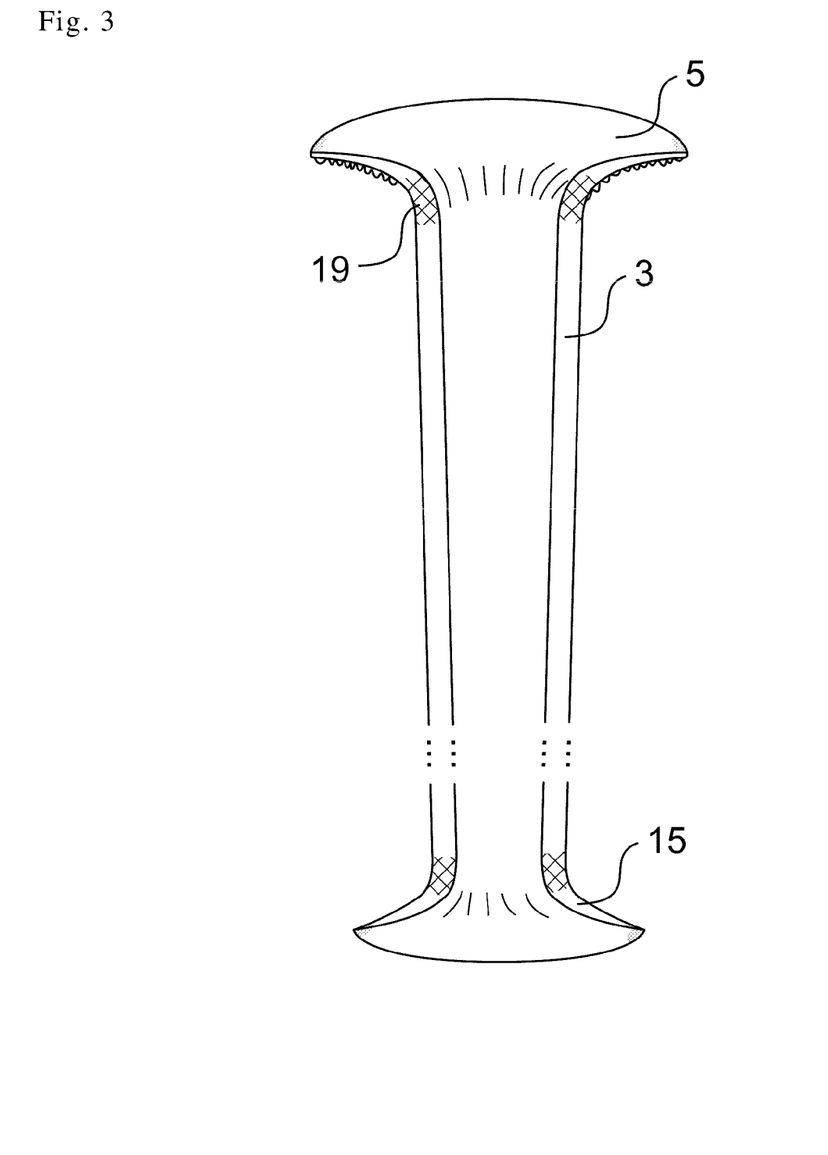
FIG. 3 is a conceptual diagram showing an example of the stent of the present invention.

FIG. 3 is a conceptual diagram showing an example of the body part and tip part of the stent. As shown in FIG. 3, the stent preferably further has a lower portion 15 located at the bottom of the body part 3. The presence of the lower portion 15 allows, for example, a nasolacrimal duct stent to prevent lacrimal reflux and reocclusion. The lower portion may have the same structure as the upper tip portion, but may have a different structure.

In the stent, the connecting part 19 that connects the body part 3 to the tip portion 5 is preferably a shape memory part.

As shown in FIG. 1, the stent has an extension part 21 extending from the lower tip portion 5, and the extension part 21 may have, at its tip, a tip part 23 that forms a curved surface and that is harder than the body part 3. The tip part 23 may have a plurality of holes or may be sealed. The sealed tip part 23 functions as a stopper. The tip part 23 and all or part of the extension part 21 may be cut and removed after the stent is placed.

A stent having such a structure can be easily placed.

Figure 4:
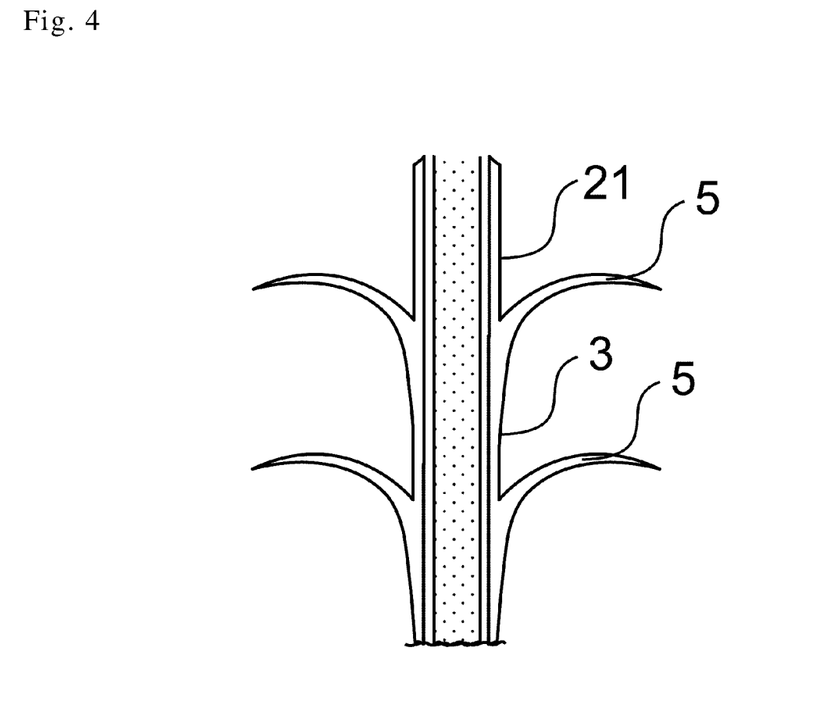
FIG. 4 is a conceptual diagram showing an example of the stent of the present invention.

FIG. 4 is a conceptual diagram showing an example of the body part of the stent. As shown in FIG. 4, the stent may have multiple stages of tip portions 5 (portions that become wider toward the tip). Particularly in this case, the tip portions 5 may also be referred to as wide portions or wing portions.

Figure 5:
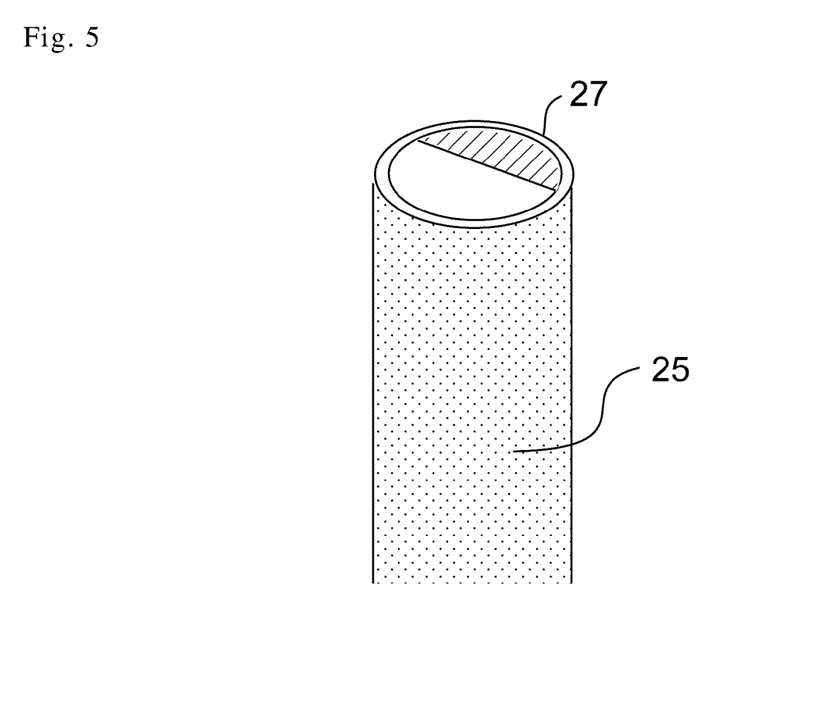
FIG. 5 is a conceptual diagram showing an example of the kit of the present invention.

FIG. 5 is a conceptual diagram showing an example of the kit of the present invention. The stent guide 25 is inserted into the body part 3 and guides the stent to the target location. The stent guide 25 has a blade 27 on the inner surface of its tip. The stent guide 25 may be a suction tube.

Figure 6:
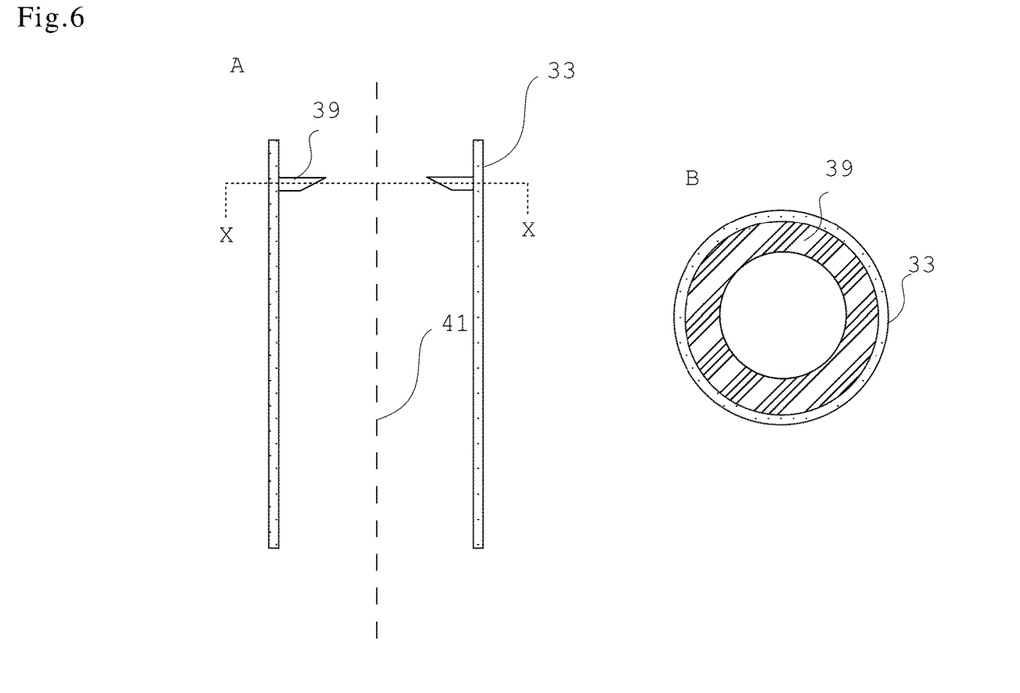
FIG. 6 is a conceptual diagram showing an example of the tip part of a suction tube.

FIG. 6 is a conceptual diagram showing an example of the tip part of a suction tube. FIG. 6A shows a cross-sectional view of the tip part of the suction tube, and FIG. 6B shows an X-X cross-sectional view of FIG. 6A. The suction tube is a medical suction tube having a tubular suction tube body part 33 and a connecting part that connects the suction tube body part 33 to a suction device. Suction tubes have suction tube body parts in various shapes, such as a tubular linear shape, a cylindrical shape with a part whose diameter decreases toward the tip, and a tubular shape with a bent part in the middle. The diameter φ of the tubular suction tube body part 33 is, for example, 0.5 mm or more and 1 cm or less, and may be 0.5 mm or more and 5 mm or less, or 1 mm or more and 3 mm or less. Since the present invention is preferably used in a minute region where it is difficult to open and close medical scissors, the diameter φ may be 0.5 mm or more and 2 mm or less. As shown in FIG. 6, a blade 39 for resecting tissue is provided inside the tip region of the suction tube body part 33. All or part of the edge (peak) of the blade 39 is preferably connected to the inner wall of the suction tube body part 33 of the suction tube. It is preferable that the part (cutting blade part) that cuts the target site, such as tissue, faces toward a central axis of the suction tube inside the suction tube. The cutting blade part may extend in the direction perpendicular to the central axis of the suction tube body part 33, or may extend at an angle upward or downward.

The pressure of the suction tube becomes negative upon suction from the suction device. Therefore, as shown in FIG. 6A, the blade 39 preferably has a taper (inclination) such that the width of the blade increases toward the tip (the upper part of the drawing) (the cutting blade part extends at an angle upward with respect to the central axis of the suction tube body part 33). The suction force can be increased by the possession of such a blade. On the other hand, as shown in FIG. 6B, when the blade has a hollow shape (a shape in which there is no blade around the central axis), there is a portion above the blade 39 where the suction from the suction device is weakened. If there is microtissue that is not desired to be sucked, the microtissue can be positioned above the blade 39, thereby protecting the tissue while sucking body fluids, which is preferable. From such a viewpoint, the blade length (blade width: distance from the inner wall of the suction tube to the blade edge) is, when the inner diameter of the suction tube is regarded as φ, is preferably 1/20 or more and 1/3 or less of φ, and may be 1/10 or more and 1/4 or less, or 1/10 or more and 1/5 or less. Since the suction tube is very small, the thickness of the blade may be adjusted accordingly. For example, the thickness of the blade may be 10 μm or more and 1 mm or less, 50 μm or more and 0.5 mm or less, or 0.1 mm or more and 0.5 mm or less. The blade 39 may be present at the tip of the suction tube, or as shown in FIG. 6A, below the tip to secure the top of the blade and avoid blade loss. The blade of FIG. 6B has a hollow circular shape. Alternatively, the blade may be chord-shaped, or may not be a perfect circle but may be in a state of being partially present, such as a distorted circle or a tooth mark.

Figure 7:
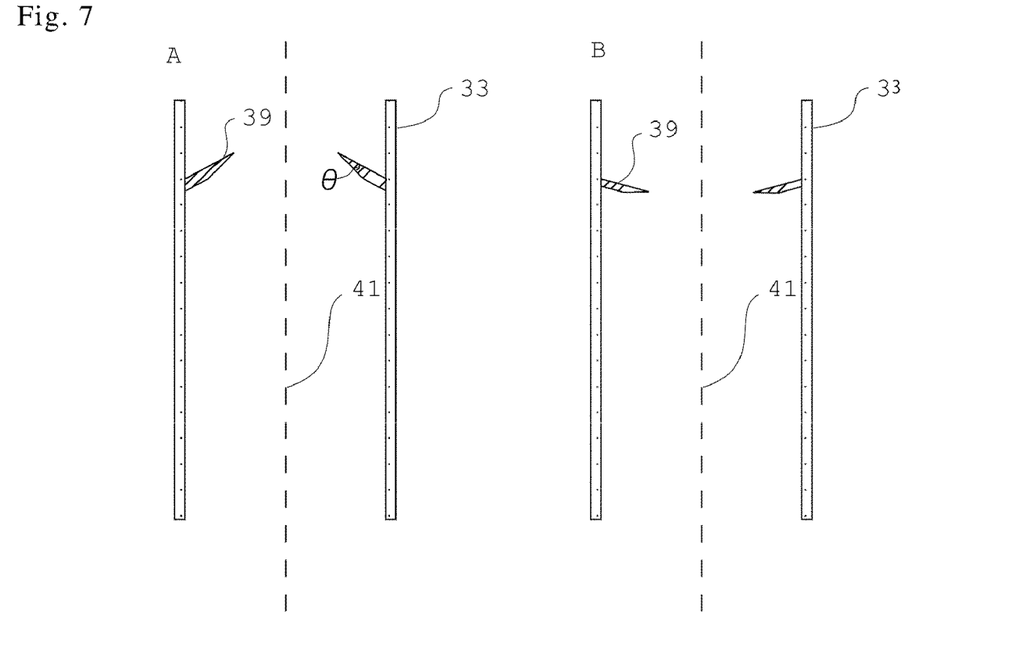
FIG. 7 is a conceptual diagram showing an example of a cutting blade part extending at an angle from the direction perpendicular to a central axis of the suction tube body part.

FIG. 7 is a conceptual diagram showing an example of a cutting blade part extending at an angle from the direction perpendicular to the central axis of the suction tube body part. FIG. 7A shows an example of a cutting blade part extending at an angle upward from the direction perpendicular to the central axis of the suction tube body part, and FIG. 7B shows an example of a cutting blade part extending at an angle downward from the direction perpendicular to the central axis of the suction tube body part. In FIG. 6, the blade 39 extends substantially perpendicular from the inner wall of the suction tube body part 33, while in FIG. 7, the blade is inclined. In FIG. 7A, θ indicates the taper angle of the cutting blade part, and θ is, for example, 1 degree or more and 45 degrees or less, and may be 5 degrees or more and 30 degrees or less, or 5 degrees or more and 20 degrees or less.

Figure 8:
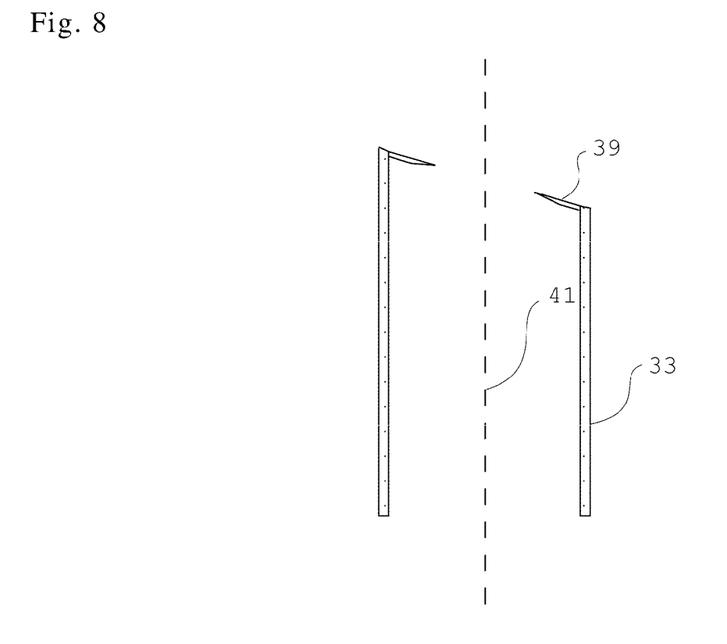
FIG. 8 is a conceptual diagram showing an example of a suction tube having a blade that is a hollow blade present inside the suction tube body part at an angle with respect to the central axis of the suction tube body part, and having an edge in contact with the inside of the suction tube body part.

FIG. 8 is a conceptual diagram showing an example of a suction tube having a blade that is a hollow blade present inside the suction tube body part at an angle with respect to the central axis of the suction tube body part, and having an edge in contact with the inside of the suction tube body part. In this example, the tip of the suction tube is cut diagonally like an injection needle, and a blade 39 is present along the cut tip. Alternatively, the tip part may be tubular. The blade 39 is a hollow blade that is present inside the suction tube body part at an angle with respect to the central axis 41 of the suction tube body part, and that has an edge in contact with the inside of the suction tube body part, whereby a small object can be easily resected. When the tip region of the suction tube body part has a shape inclined with respect to the central axis of the suction tube body part along the blade, the suction tube itself can be used like an injection needle, and the suction tube body part can be used to resect the object or to continuously suck body fluids, such as blood, while being inserted into the tissue. The inclination may have any angle. Assuming that an angle of 0 degrees is perpendicular to the central axis 11, the inclination is, for example, 1 degree or more and 70 degrees or less, and may be 5 degrees or more and 45 degrees or less, 10 degrees or more and 30 degrees or less, or 10 degrees or more and 50 degrees or less.

Figure 9:
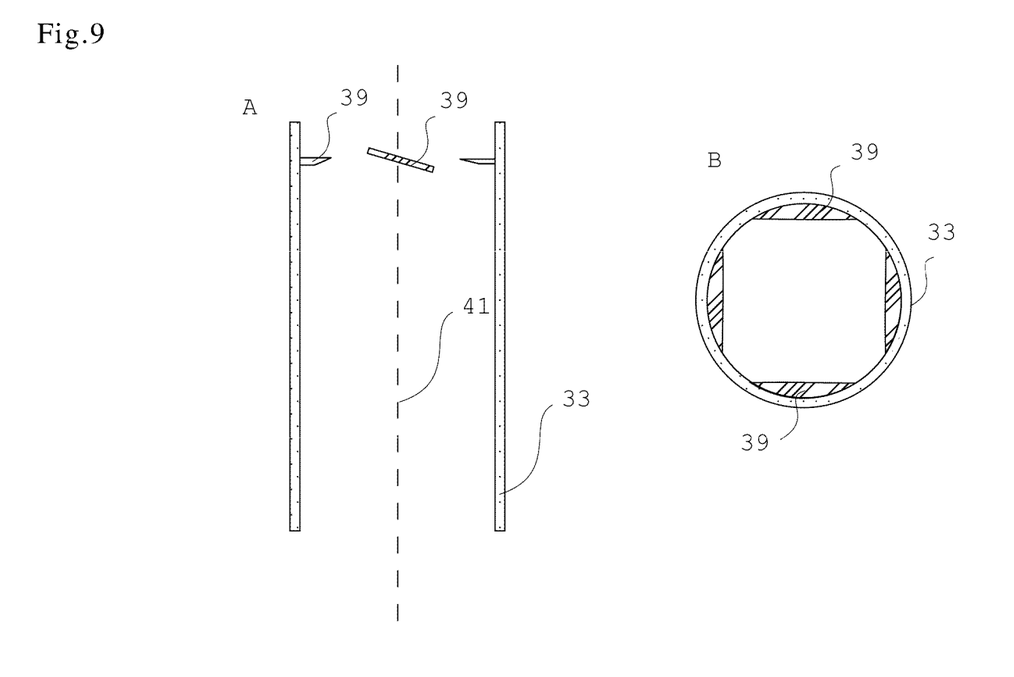
FIG. 9 is a conceptual diagram showing an example of a suction tube having a plurality of blade parts.

The edge of the blade is preferably in contact with the inside of the suction tube body part. The number of blades may be one, or there may be a plurality of blade parts. FIG. 9 is a conceptual diagram showing an example of a suction tube having a plurality of blade parts. In the example shown in FIG. 9, the blade has a plurality of blade parts with edges in contact with the inside of the suction tube body part, and the plurality of blade parts are inclined with respect to the central axis of the suction tube body part. Having such a shape makes it possible to easily resect the target tissue and the like. FIG. 9A is a conceptual diagram of the suction tube being divided in half. FIG. 9B is a view of the suction tube of FIG. 9A viewed from above. In the example of FIG. 9, four blade parts are provided every 90 degrees. The blade edges are present in parts facing toward the central axis, and the object, such as tissue, inserted into the suction tube can be resected. When the suction tube has a plurality of blades 39, the plurality of blades 39 may be inclined in the same direction (when the suction tube body part 33 is developed, the orientations of the blades 39 are approximately parallel to each other, like /,/,/,/), or the adjacent blades 39 may be inclined in opposite directions (when the suction tube body part 33 is developed, the orientations of the blades 39 are like /,\,/,\).

Figure 10:
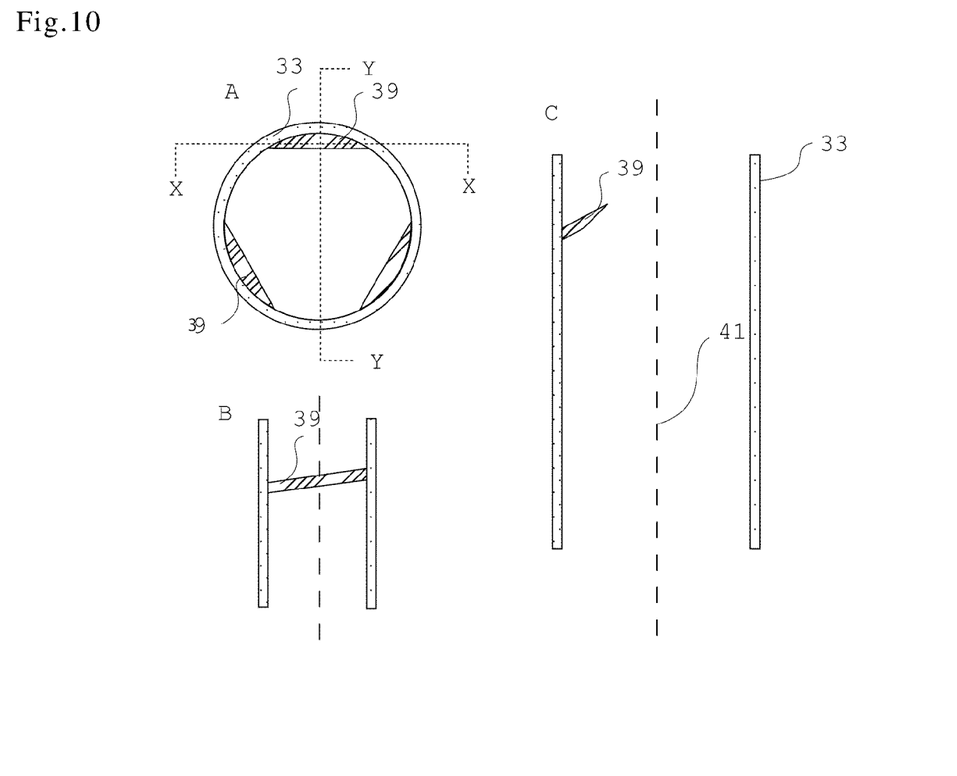
FIG. 10 is a conceptual diagram showing an example of a plurality of (three) inclined cutting blade parts extending at an angle from the direction perpendicular to the central axis of the suction tube body part.

FIG. 10 is a conceptual diagram showing an example of a plurality of (three) inclined cutting blade parts extending at an angle from the direction perpendicular to the central axis of the suction tube body part. FIG. 10A shows a conceptual diagram of the suction tube viewed from above, FIG. 10B shows an X-X cross-sectional view of FIG. 10A, and FIG. 10C shows a Y-Y cross-sectional view of FIG. 10A. When the suction tube body part of the suction tube is rotated, the target tissue can be easily resected by the cutting blade parts of the blades.

Figure 11:
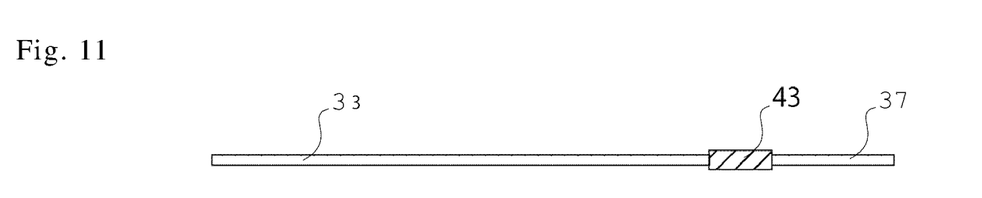
FIG. 11 is a conceptual diagram showing an example of a suction tube comprising a rotation mechanism for rotating the suction tube body part.

FIG. 11 is a conceptual diagram showing an example of a suction tube comprising a rotation mechanism for rotating the suction tube body part. The rotation mechanism is an optional element; however, the presence of the rotation mechanism has an advantageous effect as explained below. For example, the rotation mechanism 43 is hollow, and does not prevent the suction of liquid or objects by the suction tube. This suction tube may have a hole to relieve pressure. In an example of the rotation mechanism 43, when the rotation mechanism 43 is rotated with a finger or a hand using a rotation drive mechanism, such as a ball bearing, the suction tube body part 33 can be driven to rotate with respect to the connecting part, along with the rotation of the rotation mechanism. When the rotation mechanism 43 is moved with a finger, the blade rotates in accordance with the rotation of the suction tube body part of the suction tube; thus, the target tissue can be easily resected during the operation. Further, even if the suction of the suction tube is reduced during the operation, the rotation mechanism 43 can be rotated to thereby give vibration to the suction tube body part and prevent clogging, which also contributes to the efficiency of the operation. In addition, a small motor or actuator may be used to drive the suction tube body part 33 to rotate with respect to the connecting part 37. The rotation mechanism 43 is connected to a power supply, not shown, and when the practitioner turns on the power (to start the rotation operation), the rotation mechanism 43 is driven such that the suction tube body part 33 is rotated by electric power. In this way, the target tissue etc. can be effectively resected.

A preferred example of the use of the suction tube is a tissue collection device comprising the suction tube, and a solution tank that is connected to the suction tube body part 33 and that contains a sucked object. The solution tank may be connected to a hose or the like connected to the connecting part. For example, liquid and solid are centrifuged because of their different weights; thus, the liquid is sucked into the suction device, and the solid is mainly collected in the solution tank. Since the solution tank contains, for example, a tissue preservation solution, the collected tissue etc. can be analyzed.

Stents for various specific applications will be described below. Conjunctival nasal cavity stent and conjunctival lacrimal stent The total length of a conjunctival nasal cavity stent and conjunctival lacrimal stent is, for example, 0.5 cm or more and 3.5 cm or less. The total length may be 1 cm or more and 3 cm or less. The conjunctival nasal cavity stent and conjunctival lacrimal stent preferably have a mesh-like body part 3. The body part 3 may be formed by using a memory alloy, or a tip part 23 may not be provided.
Nasolacrimal Duct Stent A nasolacrimal duct stent is one of the applications in which the effect of the stent of the present invention can be most exerted. The total length of the nasolacrimal duct stent is, for example, 1 cm or more and 6 cm or less, and may be 2 cm or more and 5 cm or less. A tip part 23 may not be provided.
Monro Foramen Stent and Cerebral Aqueduct Stent The total length of a Monro foramen stent and cerebral aqueduct stent is, for example, 1.5 cm or more and 20 cm or less. The Monro foramen stent and cerebral aqueduct stent are preferably not provided with a tip part 23.
Eustachian Tube Stent The total length of a eustachian tube stent is, for example, 2 cm or more and 4.5 cm or less. The eustachian tube stent preferably has a mesh-like body part 3. The body part 3 may be formed by using a memory alloy, or a tip part 23 may not be provided.
Bile Duct Stent The total length of a bile duct stent is, for example, 2 cm or more and 15 cm or less. The bile duct stent preferably has a mesh-like body part 3. The body part 3 may be formed by using a memory alloy, or a tip part 23 may not be provided.
Pancreatic Duct Stent The total length of a pancreatic duct stent is, for example, 10 cm or more and 15 cm or less. The pancreatic duct stent preferably has a mesh-like body part 3. The body part 3 may be formed by using a memory alloy, or a tip part 23 may not be provided.
Anal Stent The total length of an anal stent is, for example, 15 cm or more and 30 cm or less. The anal stent preferably has a mesh-like body part 3. The body part 3 may be formed by using a memory alloy, or a tip part 23 may not be provided.
Ureteral Stent The total length of a ureteral stent is, for example, 15 cm or more and 30 cm or less. The ureteral stent preferably has a mesh-like body part 3. The body part 3 may be formed by using a memory alloy, or a tip part 23 may not be provided.
Fallopian Tube Stent The total length of a fallopian tube stent is, for example, 8 cm or more and 18 cm or less. The fallopian tube stent preferably has a mesh-like body part 3. The body part 3 may be formed by using a memory alloy, or a tip part 23 may not be provided.

INDUSTRIAL APPLICABILITY

The present invention can be used in the field of medical devices.

REFERENCE SIGNS LIST

3. Body part
5. Tip portion
6. Imaging unit
7. External stopper
9. Backflow prevention mechanism
15. Lower portion
19. Connecting part
21. Extension part
23. Tip part

The invention claimed is:
1. A stent comprising:
a tubular body part (3); and
a first granulation occlusion prevention part (15) that is attached to an outside surface of the body part (3) and becomes wider as a radial distance increases along a first end direction, the first granulation occlusion prevention part (15) is configured to have a wing shape and be extended radially outward from the outside surface of the body part (3), whereby the first granulation occlusion prevention part (15) has a tip end with a largest radial distance that is the largest radial distance of the entire stent;
wherein the body part (3) has a first extension part (22) extending in the first end direction from a connecting part that connects the first granulation occlusion prevention part (15) to the body part (3), the connecting part being at a crossed part of the tubular body part (3) and the first granulation occlusion prevention part (15), the first extension part (22) has a tip on which a tip part (23) is disposed, the tip part (23) forming a curved surface and being harder than the body part (3), and the tip part (23) and all or part of the first extension part (22) are to be cut and removed after the stent is placed.

2. The stent according to claim 1, wherein the first granulation occlusion prevention part (15) comprises an imaging unit (6) that allows visual recognition when imaging is performed from outside after the stent is placed inside a body.

3. The stent according to claim 1, wherein the body part (3) has a mesh-like shape.

4. The stent according to claim 1, wherein the body part (3) has one or more external stoppers (7) on its outer periphery.

5. The stent according to claim 1, wherein the body part (3) has an inner periphery on which a backflow prevention mechanism (9) is disposed, and the backflow prevention mechanism (9) is a semicircular element with a hollow inside, and an arc portion of the semicircular element is in contact with an inside of the body part (3).

6. The stent according to claim 1, wherein a connecting part (19) that connects the body part (3) to the first granulation occlusion prevention part (15) is a shape memory part.

7. The stent according to claim 1, further comprising a second granulation occlusion prevention part (5) that is attached to the outside of the body part (3) in a second end direction from the first granulation occlusion prevention part (15), the second end direction being an end direction opposite to the first end direction, the second granulation occlusion prevention part (5) becoming wider as the radial distance increases along the second end direction.

8. The stent according to claim 7, wherein the body part (3) further includes a second extension part (21) extending in the second end direction from a connecting part that connects the second granulation occlusion prevention part (5) to the body part (3).

9. A kit comprising:

the stent according to claim 1; and a stent guide (25), wherein the stent guide (25) is inserted into the body part (3) and guides the stent to a target location, and the stent guide (25) has a blade (27) on an inner surface of a tip of the stent guide (25).

10. The stent according to claim 1, wherein the stent further comprises a second granulation occlusion prevention part that is attached to an outside surface of the body part (3) and becomes wider as a radial distance increases along the first end direction, the second granulation occlusion prevention part is configured to have a wing shape and be extended radially outward from the outside surface of the body part (3), whereby the second granulation occlusion prevention part has a tip end with a largest radial distance.

* * * * *